(12) United States Patent
Cleary et al.

(10) Patent No.: US 6,817,068 B2
(45) Date of Patent: Nov. 16, 2004

(54) ADJUSTABLE LENGTH STRAP ASSEMBLY

(75) Inventors: Stephen Cleary, Waterbury, VT (US); Joshua B. Poulsen, Tooele, UT (US)

(73) Assignee: The Burton Corporation, Burlington, VT (US)

( * ) Notice: Subject to any disclaimer, the term of this patent is extended or adjusted under 35 U.S.C. 154(b) by 0 days.

(21) Appl. No.: 10/335,980

(22) Filed: Jan. 2, 2003

(65) Prior Publication Data

US 2004/0128745 A1 Jul. 8, 2004

(51) Int. Cl.[7] .............................. A61F 9/02; A44B 21/00
(52) U.S. Cl. ........................ 24/3.13; 24/3.3; 24/115 G; 351/123; 2/426; 2/452
(58) Field of Search ............................ 24/115 G, 115 R, 24/136 K, 300, 301, 3.3, 3.13; 2/452, 426; 351/123

(56) References Cited

U.S. PATENT DOCUMENTS

| | | | |
|---|---|---|---|
| 282,285 A | | 7/1883 | Dessart |
| 886,780 A | | 5/1908 | Dwyer |
| 1,153,334 A | * | 9/1915 | Oswald .................. 24/300 |
| 1,365,425 A | | 1/1921 | Shewhart |
| 1,695,747 A | | 12/1928 | Tost |
| 1,942,442 A | | 1/1934 | Motsinger |
| 2,277,994 A | | 3/1942 | Roberts |
| 2,650,400 A | | 9/1953 | Kellems |
| 2,898,596 A | | 8/1959 | Keen |
| 3,080,867 A | * | 3/1963 | Eichinger ............... 24/115 G |
| 3,397,026 A | | 8/1968 | Spina |
| 3,827,790 A | * | 8/1974 | Wenzel .................. 24/3.13 |
| 3,879,804 A | * | 4/1975 | Lawrence ............... 24/3.3 |
| 4,077,068 A | | 3/1978 | Anderson |
| 4,112,521 A | | 9/1978 | Uke |
| 4,468,819 A | | 9/1984 | Ohno |
| 4,511,225 A | | 4/1985 | Lipson |
| 4,607,398 A | | 8/1986 | Faulconer |
| 4,783,164 A | * | 11/1988 | Heiberger ............... 351/156 |
| 4,885,824 A | * | 12/1989 | Schwab et al. ............ 24/115 H |
| D319,111 S | | 8/1991 | Sandel et al. |
| 5,237,986 A | | 8/1993 | Seppala et al. |
| 5,303,428 A | | 4/1994 | Pernicka |
| 5,313,671 A | | 5/1994 | Flory |
| 5,502,844 A | | 4/1996 | Alvarado |
| 5,511,251 A | | 4/1996 | Brakas |
| 5,511,290 A | | 4/1996 | Perry et al. |
| 5,541,676 A | | 7/1996 | Pallat |
| 5,611,118 A | | 3/1997 | Bibbee |
| 5,651,146 A | | 7/1997 | Chao |
| D384,089 S | | 9/1997 | Yashiro |
| 5,697,128 A | * | 12/1997 | Peregrine ............... 24/115 G |
| 5,706,527 A | | 1/1998 | Kita et al. |
| 5,711,036 A | | 1/1998 | Kita et al. |

(List continued on next page.)

FOREIGN PATENT DOCUMENTS

| | | |
|---|---|---|
| EP | 0 732 259 | 9/1996 |
| WO | 98/38544 | 9/1998 |

*Primary Examiner*—Robert J. Sandy
(74) *Attorney, Agent, or Firm*—Wolf, Greenfield & Sacks, P.C.

(57) ABSTRACT

A variable length strap including at least one elastic cord, such as a shock or bungee cord, to adjustably secure an article to a wearer is disclosed. At least one cord lock may be provided on the elastic cord to assist with adjustment of strap length by being selectively slidable along or anchored to the cord. The length of the strap may be adjusted by selectively moving the cord lock along the elastic cord either towards or away from one side of the article. At least one end of the elastic cord may be secured to the cord lock. The elastic cord may also have at least one end secured to the article, or the elastic cord may be slidably mounted at a junction on the article. A guide may be provided on the elastic cord, with the elastic cord slidable through the guide. The guide may keep the first and second portions of the elastic cord separate from one another.

67 Claims, 8 Drawing Sheets

U.S. PATENT DOCUMENTS

| | | |
|---|---|---|
| 5,727,259 A | 3/1998 | Kawamata |
| 5,799,338 A | 9/1998 | Huang |
| 5,802,622 A | 9/1998 | Baharad et al. |
| 5,813,056 A | 9/1998 | Ambrose |
| 5,857,221 A | 1/1999 | Geneve et al. |
| 5,896,589 A | 4/1999 | Chou |
| 5,926,855 A | 7/1999 | Brodbeck |
| 5,956,778 A | 9/1999 | Godoy |
| 6,038,706 A | 3/2000 | Seiler |
| 6,067,664 A | 5/2000 | Cortes |
| 6,076,196 A | 6/2000 | Masumoto |
| 6,092,897 A | 7/2000 | Smerdon, Jr. |
| 6,105,177 A | 8/2000 | Paulson et al. |
| 6,119,277 A | 9/2000 | Chiang |
| 6,131,246 A | 10/2000 | Paulson et al. |
| 6,189,186 B1 | 2/2001 | Boden |
| 6,237,252 B1 | 5/2001 | Cook |
| 6,247,811 B1 | 6/2001 | Rhoades et al. |
| 6,341,383 B1 | 1/2002 | Beltrani |
| 6,367,091 B1 | 4/2002 | Chiang |
| 6,389,655 B2 | 5/2002 | Libecco |
| 6,405,384 B1 | 6/2002 | Chiang |
| 6,415,482 B1 | 7/2002 | Pontaoe |
| 2001/0001340 A1 | 5/2001 | Libecco |
| 2001/0034896 A1 | 11/2001 | Chiang |
| 2002/0029407 A1 | 3/2002 | Blechman |

\* cited by examiner

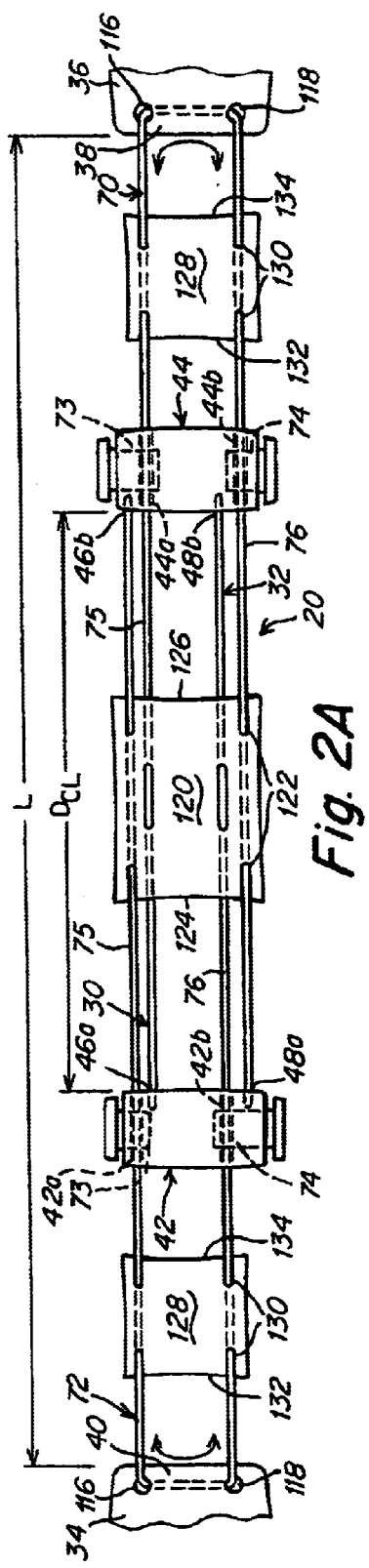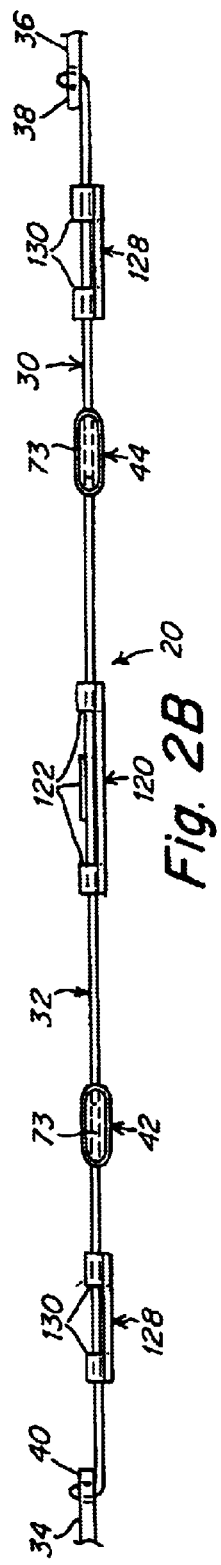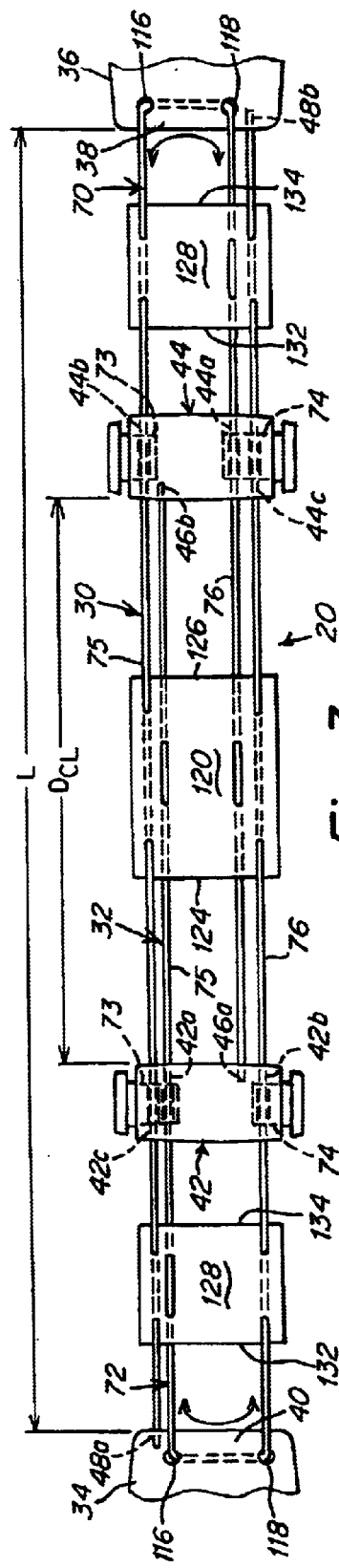

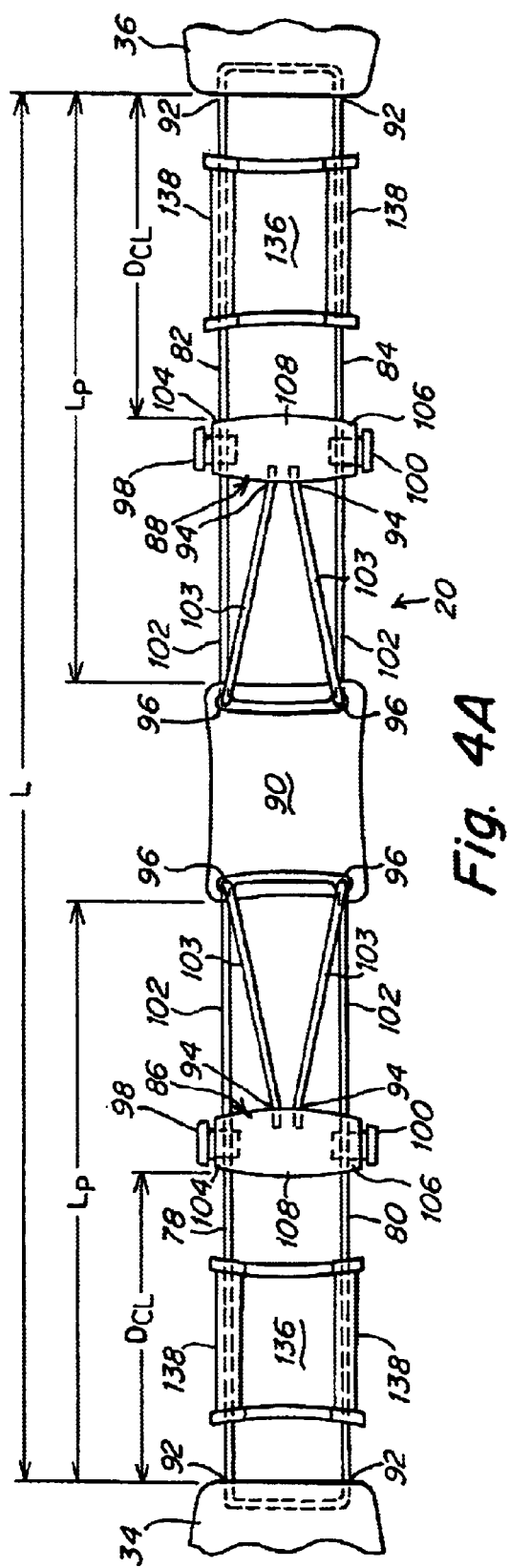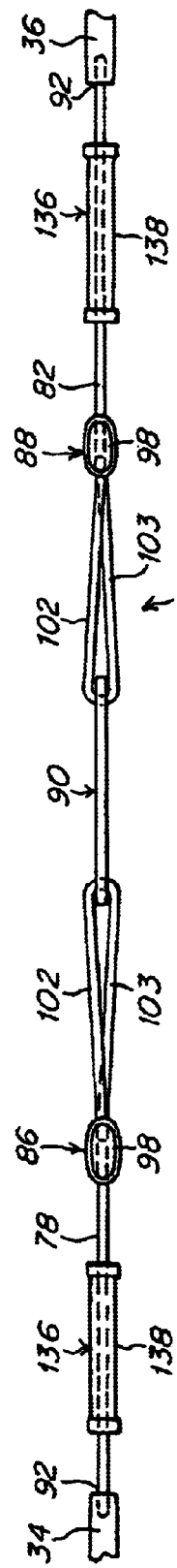
Fig. 4A
Fig. 4B

ADJUSTABLE LENGTH STRAP ASSEMBLY

FIELD OF INVENTION

The invention relates to a strap. More particularly, the invention relates an adjustable length strap assembly.

BACKGROUND OF INVENTION

Articles of wear, such as clothing, may include straps or other arrangements for securing the article to a wearer. To allow different persons to use the article and to allow the same user to adjust the comfort and feel of the article, adjustable length straps may be employed to adjustably secure the article to a wearer.

Articles of wear used in snow sports, such as goggles, snow pants, helmets, hats, gloves, coats and boots, have been provided with a wide elastic fabric strip with a length that may be adjusted by moving the elastic band through frictional buckles. Some straps, such as goggle straps, are made of two wide elastic fabric strips, each with an end secured to the goggle frame and the opposite free ends joined to buckle-type portions for connecting them together to secure the goggles to a wearer's head.

The wide fabric strip with buckles may be difficult to adjust while already on the wearer, particularly with respect to snow sports articles when the user is wearing gloves. Thus, often times one must remove her gloves and then the article to adjust the fit of the article, then put the article back on to adjust the fit, resulting in a trial and error process. Moreover, the inventors herein have recognized that the wide fabric strip band may provide little ventilation when it is placed directly on a wearer.

SUMMARY OF INVENTION

The inventors have appreciated that the length adjustment, ventilation and/or comfort of an article to be worn may be solved by providing an adjustable length strap having a cord, such as an elastic cord having a shock or bungee cord construction. This arrangement may provide better ventilation, as the cord is not as wide as a conventional fabric band and provides gaps that allow air to flow through. The strap with the cord may also feature a cord lock to assist in adjusting the size of the strap on the wearer.

In one aspect of the invention, a goggle comprises a frame and lens assembly, the assembly being breathable. The goggle further includes an adjustable length strap having at least one elastic cord with first and second ends. The elastic cord is connected to the frame and lens assembly and constructed and arranged to secure the frame and lens assembly to a head of a wearer.

In another aspect of the invention, an adjustable length strap for use with an article comprises at least one elastic cord having first and second ends, and at least one cord lock. The cord lock cooperates with the elastic cord such that the elastic cord is slidable through the cord lock to selectively adjust the length of the strap. The first and second ends of the cord are connected to the article or to the cord lock, or the first end is connected to the cord lock and the second end is connected to the article such that substantially all sections of the cord are under tension during use of the strap.

In another aspect of the invention, an adjustable length strap for use with an article comprises at least one cord having first and second ends and at least one cord lock cooperating with the elastic cord such that at least a portion of the cord is slidable through the cord lock to selectively adjust the length of the strap. At least the first end of the cord is fixed to the cord lock, while the at least one portion is slidable therethrough.

In another aspect of the invention, an adjustable length strap for an article comprises at least one elastic cord having first and second ends; and at least one cord lock cooperating with the elastic cord such that the elastic cord is slidable through the cord lock to selectively adjust the length of the strap. The cord and cord lock lie substantially within a plane that is conformable to a wearer of the article.

In another aspect of the invention, an adjustable length strap for use with an article comprises at least one elastic cord having first and second ends, at least one cord lock cooperates with the elastic cord such that the length of the strap is selectively adjustable by movement of the elastic cord through the cord lock; and a guide provided on the elastic cord. The elastic cord is movable through the guide.

In another aspect of the invention, an adjustable length strap for an article comprises at least one elastic cord having first and second ends, and at least two cord locks separated by a distance and cooperates with the elastic cord such that the elastic cord is slidable through the cord locks. The length of the strap may be adjusted by moving at least one cord lock to vary the distance between the cord locks.

In another aspect of the invention, an adjustable length strap for an article comprises at least two elastic cords having first and second ends, and at least two cord locks cooperating with the elastic cords such that the elastic cords are slidable through the cord locks to adjust the length of the strap. At least the first ends of the elastic cords are fixed to a respective cord lock and at least one segment of each cord passes through at least one cord lock.

In another aspect of the invention, a cord-type strap assembly comprises a first cord portion and a second cord portion. The first end of said first portion overlaps a second end of said second portion. The overlapping portion defines a selectively variable length.

In another aspect of the invention, a strap assembly comprises a cord-type strap having a first portion extending between a first junction and a second junction, and a second portion extending from said second junction towards said first junction. A cord lock is attached to the second portion and is mounted for movement to the first portion. The cord lock is moveable along the first portion towards and away from the first junction to adjust a length of the cord-type strap between the first junction and the second junction.

In another aspect of the invention, a strap assembly comprises a cord-type strap having a first portion extending between a first junction and a second junction, and a second portion extending between a third junction and a fourth junction. The second portion is located between the first junction and the second junction. Adjustment of a length of the second portion causes an adjustment of a length of the first portion. The first portion gets shorter as said second portion gets longer.

BRIEF DESCRIPTION OF DRAWINGS

The objects, advantages and features of this invention will be more clearly appreciated from the following detailed description, when taken in conjunction with the accompanying drawings, wherein like numbers are used for like features, in which:

FIG. 2A is a front elevational view of the strap of FIG. 1 according to one embodiment of the invention;

FIG. 2B is a top plan view of the strap of FIG. 2A;

FIG. 3 is a plan view of an adjustable length strap according to another embodiment of the invention;

FIG. 4A is a front elevational view of an adjustable length strap according to yet another embodiment of the invention;

FIG. 4B is a top plan view of the strap of FIG. 4A;

DETAILED DESCRIPTION

Figure 1:
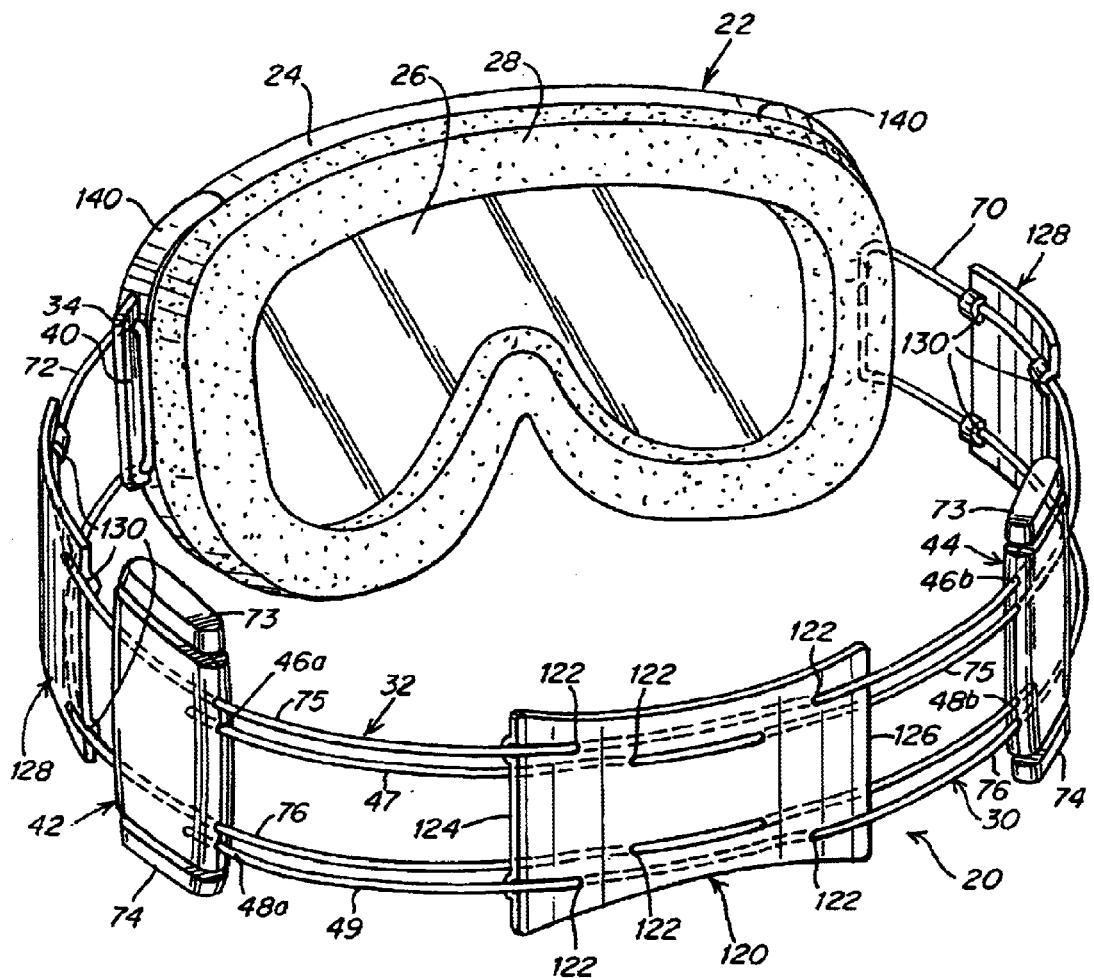
FIG. 1 is a perspective view of an adjustable length strap according to one embodiment of the invention when used on an article, such as a goggle.

The present invention is directed to an adjustable length strap. The strap may include an elongated cord, such as an elastic shock or bungee cord. The cord may be adjusted to shorten or lengthen the overall strap length. A cord lock that is selectively anchored to or moveable along the cord may be employed to hold the cord at a desired length. The strap may be used with articles to selectively secure the article to a wearer. In this manner, the cord may be adjusted to shorten or lengthen the overall strap length to thereby tighten or loosen the article to the wearer.

This arrangement of an adjustable length strap having a cord and a cord lock allows for adjustment of the strap while the article is on the wearer, even while wearing gloves. Moreover, the strap may have two slidable points of connection for the elastic cord on the article, allowing upper and lower portions of the elastic cord to be separated from one another at the connection point on the article, which may assist the wearer in adjusting the fit of the strap. Additionally, a guide positioned on the strap may keep portions of the elastic cord separated from one another, which may also assist the wearer in adjusting the fit of the strap while wearing the article and prevent tangling of the cord portions.

In one embodiment, a first end of the cord may be secured to a first junction on the article, passed through a cord lock, looped at a second junction on the article, then secured back and fixed to the cord lock. In this arrangement, as the cord lock is moved toward the first position on the article, the strap length is shortened. If the cord lock is moved toward the second position on the article, the strap length is lengthened.

In another embodiment, two cords and two cord locks may form the adjustable length strap. An end of each cord is attached to a respective cord lock and then passed through the other cord lock and looped around a junction at an end of the article and then back through the other cord lock until it is again fixed to the first cord lock. By moving the cord locks away from one another, the strap length is shortened, while moving them towards one another the strap length is lengthened.

The strap may also include additional features to render it more conformable to a wearer. In one embodiment, the ends of the cord are fixed to the article, to the cord lock or to both such that there are no free ends of the cord. In this manner, substantially the entire cord may be placed under tension during use and there are no loose ends. Another feature to render the strap more conformable includes positioning the cord(s) and cord locks(s) substantially within the same plane.

The cord lock may be any suitable device, as the present invention is not limited in this respect. As will be explained in more detail below, the cord lock has at least one push-button or plunger type lock. The length of the strap is adjustable by allowing the cord to slide though the cord lock by selectively actuating the cord lock. Once the desired length is obtained, the plunger pinches the cord against the cord lock body, for example, to hold the cord in place. The cord lock is constructed and arranged on the strap so as to be adjustable by the wearer when worn and may even be adjusted while wearing gloves or mittens.

The strap described herein can be used to secure any article, as the present invention is not limited in this respect. In one embodiment, the strap is employed with eyewear, and in particular goggles such as snow sports goggles. Alternatively, the strap may be employed as other types of straps with other articles such as belts or suspenders for pants; chin straps for helmets, caps and hats; wrist straps for gloves and mittens; wrist, waist or hood straps for coats, jackets, vests and parkas; straps for boots, shoes and bindings; or straps for luggage. Although, illustrative embodiments of the invention are described below with reference to a goggle having a single lens and a goggle frame having a pivotable arm, it should be understood, however, that the various aspects of the invention are not limited to use in the particular goggle embodiments described, but instead may be used with any suitable goggle type, such as those with two or more lenses mounted to a frame, with or without a face gasket, and those without a pivotable arm extending from the goggle.

Referring now to FIG. 1, an illustrative embodiment of a variable length strap 20 in accordance with the invention provided on an article, such as a goggle 22, is shown. The illustrated goggle 22 is shown for illustrative purposes only. Although a particular goggle is shown, it will be appreciated that the strap may be used with any type of article, including any type of goggle or eyewear. The goggle 22 includes a goggle frame 24, a lens 26 held in place by the goggle frame to form a frame and lens assembly, and a face gasket 28 to fit the goggle comfortably against the wearer's face.

The strap 20 includes at least one elongated elastic cord and preferably, two cords 30 and 32, and may be in the form of a shock or bungee cord or other stretchable cord material. The cord is connected to the goggle, for example at the first and second ends 34 and 36 of the frame 24. The cord may be adjusted to decrease or increase the overall strap length L (see FIG. 2A) to tighten or loosen the goggles. Alternatively, the cord may be looped at junctions 38 and 40 of the goggle frame 24, such that the cord is slidable through the goggle frame. Cord locks 42 and 44 may be provided on the cord to hold the cord at a desired length. For example, the cord lock may be selectively actuated to allow the cord to slide through the cord lock until a desired strap length L is achieved. When not actuated, the cord locks 42 and 44 are anchored to the cord. The cord lock(s) may be any suitable cord-locking device, which will be discussed in more detail below.

Different embodiments for the strap are shown in FIGS. 2–5D. It will be understood that the embodiments are shown for illustrative purposes only and are not intended to be limiting.

The strap 20 illustrated in FIGS. 1–2B will now be discussed. The strap 20 includes two cords 30 and 32 and two cord locks 42 and 44. A first end 46a of the first cord 30 is fixed to a first cord lock 42. The second end 48a of the cord passes through opening 44a in the second cord lock 44 and looped at a junction 38 at the second end 36 and then fed back through opening 44b in the second cord lock 44 and fixed to the first cord lock 42. A first end 46b of the second cord 32 is fixed to the second cord lock 44. The second end 48b of the second cord 32 passes through opening 42a in the first cord lock 42 and is looped at junction 40 at a first end 34 and then fed back through opening 42b in the first cord lock 42 and fixed to the second cord lock 44. Thus, two separate loops 70 and 72 are formed by the first and second cords with the first and second cord locks 42 and 44. The cords 30 and 32 do not have any free ends that extend from the strap, such that the entire length of the cords may be placed under tension during use. As shown in FIG. 2B, the cords 30 and 32 and locks 42 and 44 may be located substantially within a same plane and conformable to at least a portion of a wearer.

Upon actuation of the cord locks 42 and 44, the cords 30 and 32 may slide through the cord locks. The cord locks 42 and 44 each include two locking portions 73 and 74 to control two cord segments 75 and 76 passed through the cord locks 42 and 44. The locking portions 73 and 74 may be actuated to allow the cord locks 42 and 44 to slide upon the top and bottom cord segments 75 and 76. Typically, both locking portions 73 and 74 of each cord lock are actuated simultaneously to allow the top and bottom cord segments 75 and 76 to slide together. As shown, the cord segments 75 and 76 and other portions of the cord may be substantially parallel to one another.

In this embodiment, the length of the strap L is adjusted by varying the distance $D_{CL}$ between the cord locks. By moving the cord locks away from one another, thereby increasing the distance $D_{CL}$ between the cord locks, the strap length L is shortened. By moving the cord locks toward one another, thereby decreasing the distance $D_{CL}$ between the cord locks, the strap length L is lengthened. If only one cord lock is actuated while loosening, slack is formed but not relieved, so the strap length L does not increase. If only one cord lock is actuated while tightening, movement of the cord lock is impeded unless the other cord lock is actuated to allow the first cord lock to move. Thus, it is desirable to actuate both cord locks of this embodiment simultaneously. It will be appreciated that numerous other arrangements for the strap are possible using two or more cords and cord locks, examples of which will now be discussed.

Referring to FIG. 3, the embodiment of the strap 20 is similar to that shown in FIG. 2 and includes two cords 30 and 32 and two cord locks 42 and 44. A first end 46a of the first cord 30 is fixed to a first cord lock 42. The second end 48a of the cord passes through opening 44a in the second cord lock 44 and looped at a junction 38 at the second end 36 and then fed back through opening 44b in the second cord lock 44, back through an opening 42c in the first cord lock 42 and fixed to the first end 34 of the article. A first end 46b of the second cord 32 is fixed to the second cord lock 44. The second end 48b of the second cord 32 passes through opening 42a in the first cord lock 42 and looped at junction 40 at a first end 34 and then fed back through opening 42b in the first cord lock 42, back through an opening 44c in the second cord lock 44 and fixed to the second end 36 of the article. The strap functions similarly to the embodiment of FIG. 2 by adjusting the distance $D_{CL}$ between the cord locks. For example, when the cord locks 42 and 44 are moved towards one another the strap is lengthened and when they are moved away from one another the strap is shortened.

Figure 4C:
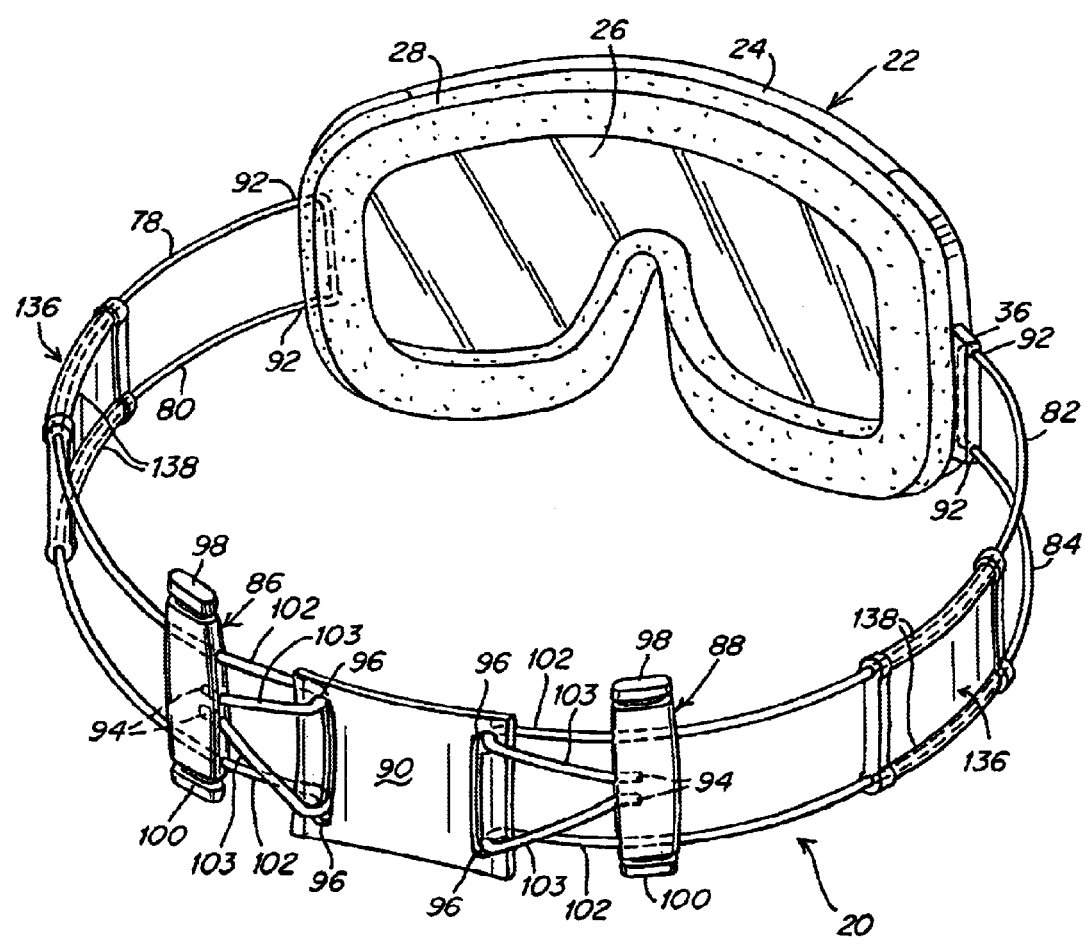
FIG. 4C is a perspective view of the strap of FIG. 4A when used on an article, such as a goggle.

FIGS. 4A–4C illustrates yet another embodiment of the strap 20 according to the invention. The strap includes four elongated cord segments 78, 80, 82 and 84 and two cord locks 86 and 88. The cord segments may include individual cords or may be formed as cord loops. That is, cord segments 78, 80 may form a single cord, as shown. Alternatively cord segment 78 may be independent cord from cord segment 80. A guide 90 is provided between the cord locks to keep the cords under tension. Each cord has a first end 92 fixed to one end 34 and 36 of the article, the second end 94 of each cord passes through an opening in the respective cord lock 86 and 88, to the guide 90 where it is looped through an opening 96 in the guide 90 and looped back on itself and is fixed to the respective cord lock. As shown in FIG. 4B, because the cords are looped back on themselves, the cords and cord locks may not lie within the same plane.

Each cord lock 86 and 88 has two locking portions 98 and 100, each to control a segment 102 of each cord. The first and third cords 78 and 82 pass through openings in the top portion 104 of the cord locks, while the second and fourth cords 80 and 84 pass through openings in the bottom portion 106 of the cord locks. The second end 94 of each cord is fixed to a middle portion 108 of the cord locks. It is to be appreciated that the cords may pass through or may be fixed to any suitable portion of the cord locks. As shown, the cord segments 102 are parallel to one another, while other cord portions 103 extending from the guide 90 to the cord locks 86 and 88, are not parallel to the cord segments 102.

In the embodiment of FIGS. 4A–C, the cord locks 86 and 88 may be actuated individually to shorten or lengthen the portion of strap $L_P$ between the guide and article to adjust overall strap length L. Typically, however, the locking portions 98 and 100 on each cord lock are actuated simultaneously. To lengthen the strap portion, the cord lock 86 and 88 is moved toward the guide 90 to increase the distance $D_{CL}$ and increase the strap length $L_P$. To shorten the strap portion, the cord lock 86 and 88 is moved away from the guide 90 to decrease the distance $D_{CL}$ and decrease the strap length $L_P$. It is to be appreciated that this embodiment could include just two straps, one on each side of the guide 90, or even more than four straps. For example, just one of the straps 78, 80 and 82, 84 may be used on either side of the guide. Alternatively, the two straps on either side of the guide may be formed as single straps that are looped through a junction at the side of the article, as shown in FIG. 4C.

Figure 5A:
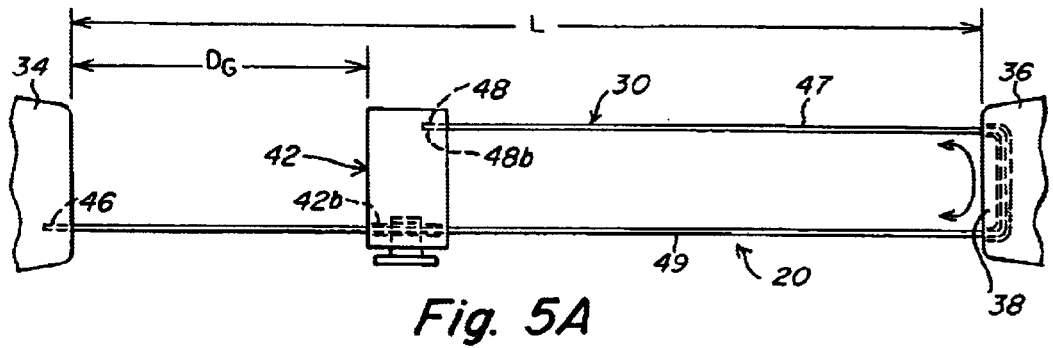
FIGS. 5A–5D are schematic views of different embodiments of a strap according to the invention.
Figure 5B:
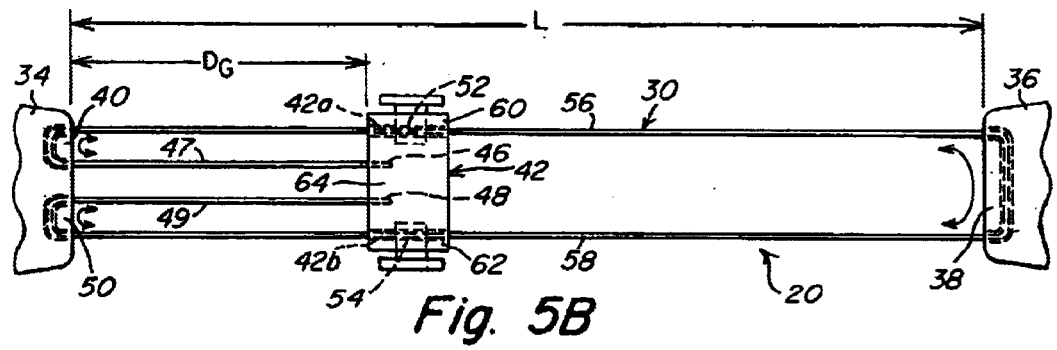
Figure 5C:
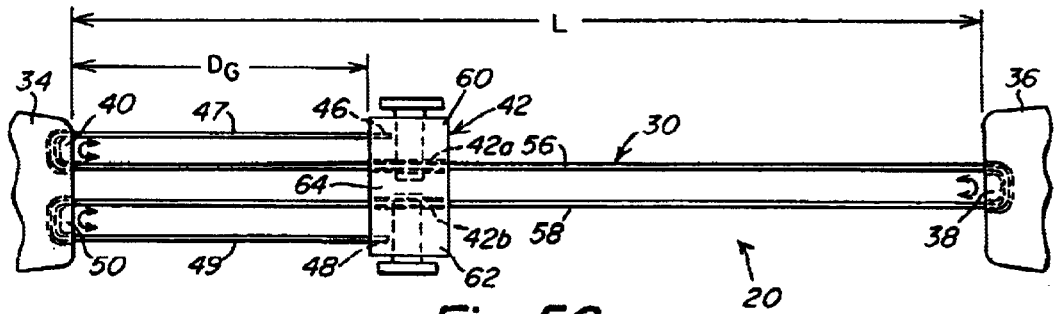

Referring now to FIGS. 5A–5C, embodiments for the strap 20 having one cord 30 and one cord lock 42 will be discussed. In FIG. 5A, a strap 20 is illustrated having an elongated cord 30 and a cord lock 42. A first end 46 of the cord is fixed to a first end 34 of the article, the second end 48 of the cord passes through opening 42b in the cord lock 42, and then looped at a junction 38 of a second end 36 of the article and then fixed back to the cord lock 42 at termination point 48b. As shown, the cord 30 may have portions 47 and 49 that are substantially parallel to one another. However, it will be appreciated that these portions may be arranged such that they are not parallel to one another, as the present invention is not limited in this respect.

In this arrangement, the cord lock 42 may be actuated to allow the cord lock to slide along the cord 30 to adjust the strap length L. If the cord lock is slid towards the first end 34, thereby reducing the distance $D_G$ between the cord lock and the first end 34, the strap length L is shortened. If the cord lock is slid toward the second end 36, thereby increasing the distance $D_G$ between the cord lock and the first end 34, the strap length L is lengthened.

In a slightly different embodiment (not shown), the second end 48 of the cord 30 may pass through the upper portion of the cord lock 42 instead of being fixed directly thereto at termination point 48b on the cord lock. Thereafter, the second end 48 may be looped at a junction of the first end and then secured back to the cord lock. In this version, the strap would be shortened or lengthened in a similar manner to the embodiment illustrated in FIG. 5A.

Another embodiment of the strap 20 having an elastic cord 30 and a cord lock 42 is illustrated in FIG. 5B. The first end 46 of the cord 30 is fixed to a side of the cord lock 42. The second end 48 of the cord is then looped at a junction 40 of the first end 34 and passed back through the cord lock 42 through an opening 42a. The cord is then looped at a second junction 38 at the second end 36, back through opening 42b of the cord lock 42 and looped at a third junction 50 at the first end 34 and fixed back to the cord lock. In this arrangement the cord lock includes two locking portions 52 and 54 to control two cord segments 56 and 58 passing through the cord lock 42. The locking portions 52 and 54 of the cord lock may be actuated to allow the cord lock 42 to slide along the top and bottom cord segments 56 and 58.

If the cord is slid toward the first end 34, thereby reducing the distance $D_G$ between the cord lock and first end, the strap length L is lengthened. If the cord lock is slid toward the second end 36, thereby increasing the distance $D_G$ between the cord lock and the first end, the strap length L is shortened. As in the embodiment discussed above, the cord may have portions 47 and 49 that are substantially parallel to one another.

The embodiments of FIGS. 5B and 5C are similar to one another, except for the position of the cord segments 56 and 58 passing through the cord lock 42 and the position of the ends 46 and 48 of the cord fixed to the cord lock. In FIG. 5B, the cord segments 56 and 58 pass through top and bottom portions 60 and 62 of the cord lock, while the ends 46 and 48 are secured to a middle portion 64 of the cord lock. Alternatively, in FIG. 5C, the cord segments 56 and 58 pass through the middle portion 64 of the cord lock, while the ends 46 and 48 are fixed to the top and bottom portions 60 and 62 of the cord lock. The embodiment of FIG. 5C functions in a similar manner to FIG. 5B to shorten or lengthen the strap 20. Because the cord segments 56 and 58 between the first end 34 to the second end 36 are spaced farther apart from one another in FIG. 5B, this embodiment may provide a more stable strap arrangement than that illustrated in FIG. 5C.

It will be appreciated that other configurations are possible, for example the location of the cord lock openings through which the cord passes and the fixed positions of the cord ends may be varied. In another embodiment, the cord segments 56 and 58 may pass through the top portion and the middle portion of the cord lock, and the ends 46 and 48 of the cord may be fixed the bottom portion and the middle portion of the cord lock. It is to be appreciated that the location of the cord lock openings through which the cord passes and the fixed positions of the cord may be placed at any suitable location on the cord lock, as the present invention is not limited in this respect.

Figure 5D:
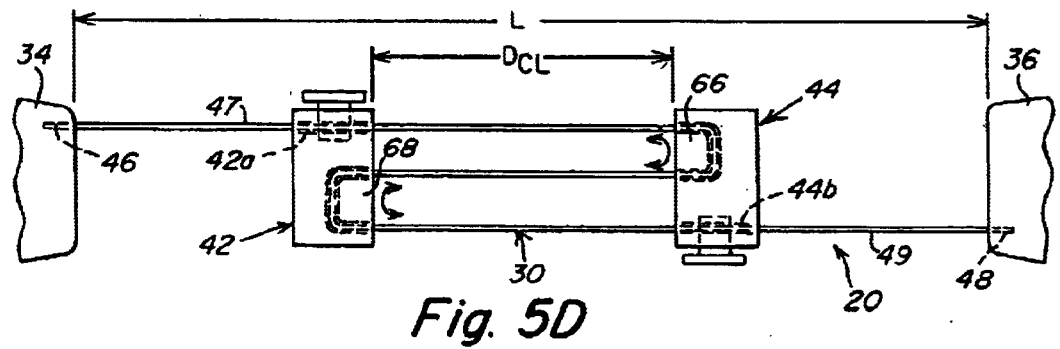

Referring now to FIG. 5D, a strap 20 is illustrated having an elongated cord 30 and two cord locks 42 and 44. A first end 46 of the cord is fixed to the first end 34, the second end 48 of the cord passes through opening 42a in the first cord lock 42 and is looped at a junction 66 in the second cord lock 44, and fed back to the first cord lock 42 where it is looped again at a second junction 68 and passes through opening 44b in the second cord lock 44 and then fixed to the second end 36. Once again, portions 47 and 49 of the cord may be substantially parallel to one another.

In this arrangement, the length of the strap L is adjusted by varying the distance $D_{CL}$ between the cord locks. If the cord locks 42 and 44 are slid towards one another, thereby decreasing the distance $D_{CL}$ between the cord locks, the strap length L is lengthened. If the cord locks are slid away from one another, thereby increasing the distance $D_{CL}$ between the cord locks, the strap length L is shortened.

As explained above, the cord 30, 32, 78, 80, 82 and 84 may be an elongated elastic cord such as a shock or bungee cord. The cords are typically made of an elongated elastic core and a stretchable mesh cover. The cord illustrated has a circular cross-section; however, the elastic core may have any suitable shaped cross-section, such as rectangular and trapezoidal cross-sections. The elastic core may be made of any elastomeric compound which provides sufficient strength and durability. Preferably the core is made up of interwoven strands. The core is encased in a tubular mesh cover to protect the elastic core. The cover is flexible and by reason of its mesh construction can stretch or lengthen as the elastic core lengthens. The cover made be made of any suitable material such as nylon. The diameter of the cord may be any suitable diameter to form the strap. It is to be appreciated that the cord may be made of any suitable construction or materials, including elastomeric and non-elastomeric materials.

The cord lock 42, 44, 86 and 88 may be any suitable mechanism that is selectively actuatable to allow the mechanism to slide along the cord, and to be anchored to the cord when not actuated. The cord lock may include a toggle having at least one locking portion. As is known in the art, the cord lock may include a housing and a plunger or pushbutton. The housing may include at least one throughole and the plunger may include a throughole to receive the cord. A spring or other biasing member connects the housing and plunger. The plunger is normally biased by the spring such that the throughholes are not aligned. To align the throughholes such that the cord lock may slide on the cord, the plunger must be depressed. When the plunger is released the sections of the cord passing through the throughholes are frictionally gripped and locked in their respective positions as the spring applies a force to misalign the throughholes.

As described above, in some embodiments more than one locking portion on the cord lock may be necessary. For example, in FIGS. 1, 2A, 3 and 4A, locking portions include a push button lock on both ends of the cord lock to cooperate with two segments of cord that are passed through the cord lock. The dual push button locks may function similarly to the locks described above. In one embodiment, each locking portion may be actuated independently such that each has its own plunger. Alternatively, a single plunger may actuate both locking portions.

Figure 6A:
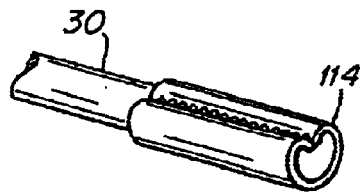
FIG. 6A is a perspective view of an elastic cord and ferrule according to an embodiment of the invention.
Figure 6B:
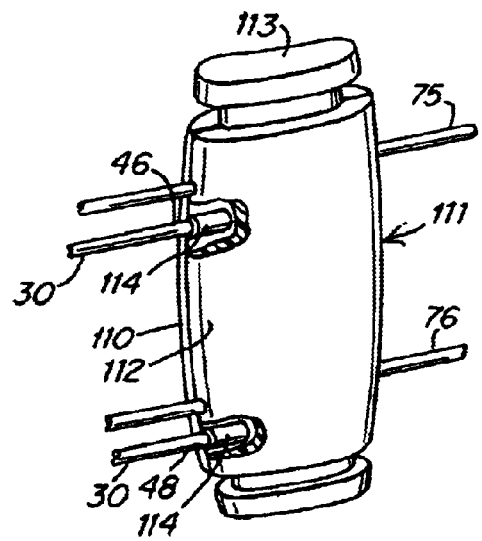
FIG. 6B is a perspective view of a cord lock and the elastic cord of FIG. 6A according to an embodiment of the invention.

Referring specifically to FIGS. 6A–6B, a particular embodiment of an end 46 and 48 of the cord and a portion of the cord lock 42, 44, 86 and 88 is shown. In this embodiment, the cord lock includes two halves 110 and 112 that snap-fit together. It is to be appreciated that the cord locks may be made by any suitable method from any suitable material. To keep the cord intact, a ferrule 114 is crimped on the end 46 and 48 of the cord securing both the strands and the cover of the cord. The ferrule 114 may be made of any suitable material, such as metal. The ferrule and the end of the cord are then placed in one of the cord lock halves 110 in the desired position and the other half is snap-fit onto the first half, thereby fixing the end of the cord with the ferrule within the cord lock. A similar construction may be used to fix the end of the cord to the goggle ends 34 and 36. The ends of the cord may also be glued, molded or otherwise fixed to either the cord lock or goggle.

Figure 6C:
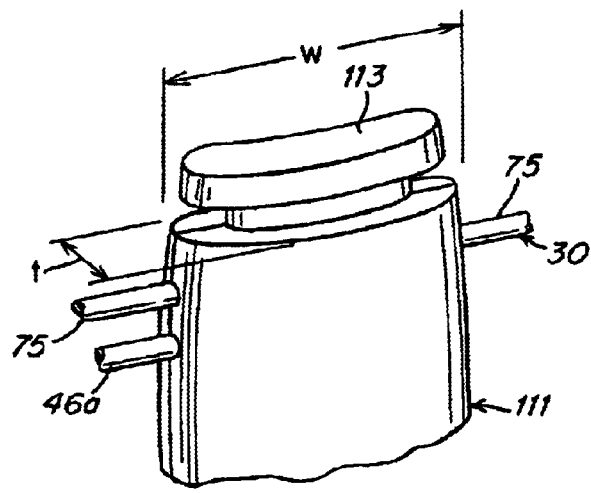
FIG. 6C is a perspective view of a portion of the cord lock according to an embodiment of the invention.

In one embodiment, the cord lock 42 is elongated and flattened, as shown in FIG. 6C, such that it can lie generally flat against a wearer. As shown in FIG. 6C, the cord lock 42 includes a body 111 and a plunger 113. The body 111 has a thickness t and a width w, with the thickness t being less than the width w.

As also described, the cord 30 and 32 may be connected to the article or the cord lock by looping the cord at a junction in the article or the cord lock. A shown in FIG. 8, the article may include two holes 116 and 118 through which the cord passes, such that the cord is moveable through the article end 34 and 36. A similar moveable loop may be formed in the cord lock. Alternatively, the loop may be enclosed within the article or the cord lock. It is to be appreciated that the cord may be slidably looped through the article or cord lock in any suitable manner, as the present invention is not limited in this regard.

Figure 7:
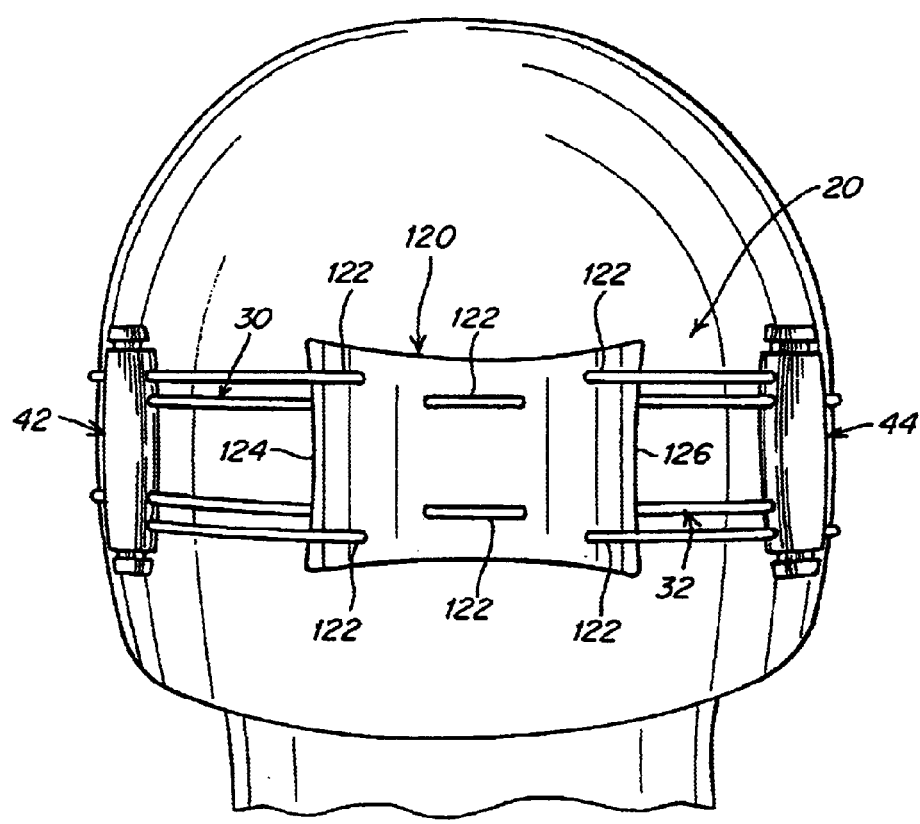
FIG. 7 is a back view of the goggle and strap of FIG. 1 on the head of a wearer.

FIGS. 1 and 7 illustrate a guide 120 which may be provided on the cords such that the guide is slidable on the cord. The guide 120 includes dedicated bores or other guide elements 122 to direct the cord between the cord locks and prevent tangling of the cord portions with one another. The cords essentially pass from a first side 124 of the guide to a second side 126 of the guide. A different embodiment of the guide 90 is shown in FIG. 4, the guide 90 includes openings 96 through which the cords pass. Because the cord passes from the cord lock to the guide, through the bore and back to the cord lock, the cord partially overlaps on itself.

Figure 8:
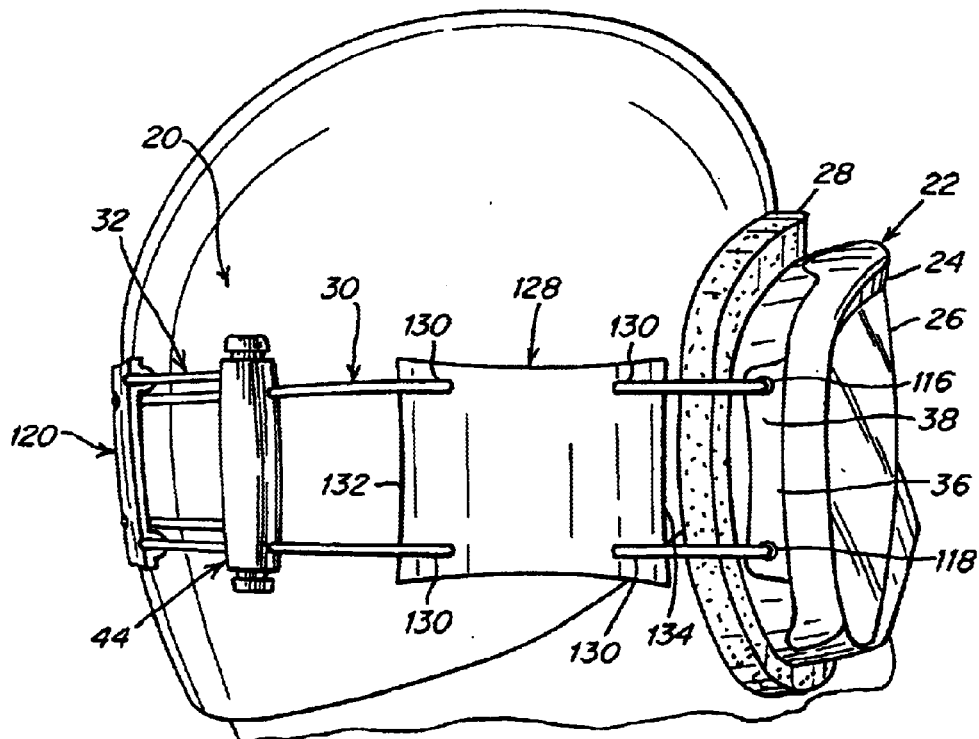
FIG. 8 is a side view of the goggle and strap of FIG. 1 on the head of a wearer.

As shown in FIG. 8, side guides 128 may also be provided to direct the cords from the article ends to the cord locks. The side guides may be moveable on the cord. The side guides 128 also include dedicated bores or other guide elements 130, for example to allow the cord to pass from a first side 132 of the side guide to a second side 134 of the side guide.

The guide 120 and 90 and side guide 128 may be made of any suitable material, including urethane. It will also be appreciated that the guide and side guide may be rigid, flexible or a combination of both.

In an alternative embodiment shown in FIG. 4, sleeves 136 may be provided over the cords. The sleeve may have an elongated tube 138 to receive the cord and direct the cord from the article to the cord lock. The sleeve may be made of any suitable material, such as neoprene.

As discussed above, the strap may be used with a variety of articles including eyewear, including goggles; belts or suspenders for pants; chin straps for helmets, caps and hats; wrist straps for gloves and mittens; wrist, waist or hood straps for coats, jackets, vests and parkas; straps for boots, shoes, and bindings; or straps for luggage. Although the strap has been illustrated with a goggle, this is not intended to be limiting.

Moreover, although a particular goggle is illustrated, it will be appreciated that any goggle may be used, although, in one embodiment, the inventive strap is used with snow goggles. Snow goggles, such as ski and snowboarding goggles are typically breathable, unlike other goggles such as swim goggles. The breathability may be provided in any suitable manner, such as by holes or other openings in the lens, frame or face gasket. Typically, the holes or openings are covered by a foam or sponge-like material that allows air to circulate within the goggle, but may prevent snow or other liquid from entering. The breathability assists in preventing condensation from forming on the inside of the goggle lens, which may obstruct the wearer's sight.

Figure 9A:
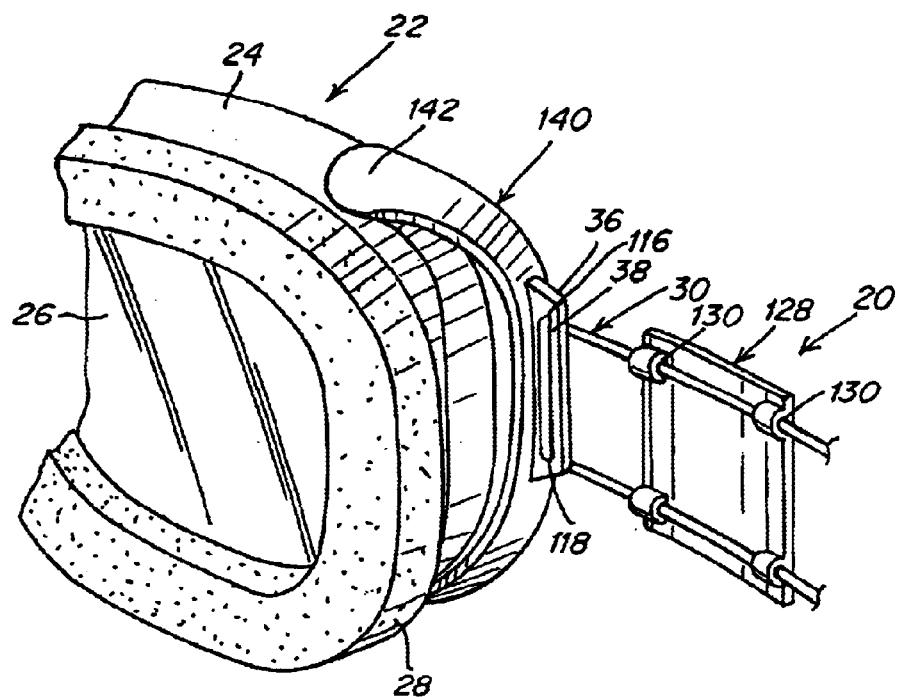
FIG. 9A is a detailed view of the pivotable arm of the goggle of FIG. 1 in an open position.
Figure 9B:
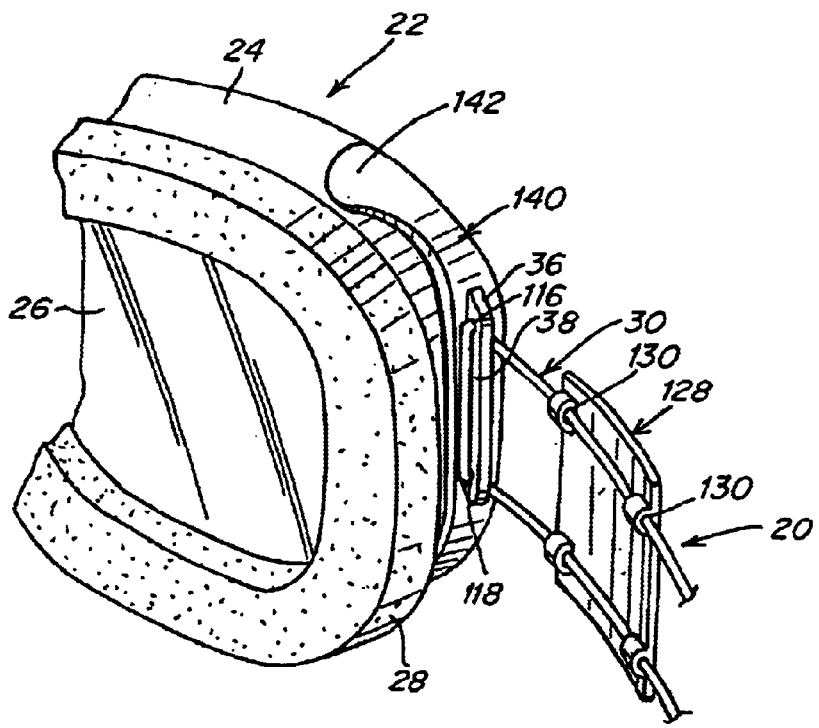
FIG. 9B is a detailed view of the pivotable arm of the goggle of FIG. 1 in a closed position.

Referring now to FIGS. 1, 9A and 9B, the particular goggle illustrated includes a frame 24 having arms 140 at the sides 34 and 36 of the goggle that are pivotably connect to the frame at a pivot point 142. The arm 140 is shown in FIG. 9A in an outwardly pivoted position and is shown in a closed position in FIG. 9B. The pivotable arm is discussed in more detail in co-pending application Ser. No. 10/008,357, assigned to The Burton Corporation. As illustrated, the cord 30 and 32 may be looped through a junction 38 and 40 at the pivotable arm 140. Alternatively, the ends 46 and 48 of the cord 30 and 32 may be secured directly to the pivotable arm 140.

It will also be appreciated that the cord 30, 32, 78, 80, 82 and 84 may not be connected to the eyewear or other article. Instead, an intermediate device may be used to connect the cords to the eyewear or other article.

Having described certain embodiments of the present invention, various alterations, modifications, and improvements will readily occur to those skilled in the art. It should be understood that structure and composition of the adjustable length strap and article can vary from the illustrative embodiments described above. Therefore, such alterations, modifications and improvements are intended to be within the spirit and scope of the invention. Accordingly, the foregoing description is by way of example only, and not intended to be limiting. The scope of this invention is defined only by the following claims and their equivalents.

What is claimed is:

1. An adjustable length strap for use with an article, the strap comprising:
   at least one elastic cord having first and second ends;
   at least one cord lock cooperating with the elastic cord such that the elastic cord is slidable through the cord lock to selectively adjust the length of the strap, the first and second ends of the cord are connected to the article or to the cord lock, or the first end is connected to the cord lock and the second end is connected to the article such that substantially all sections of the cord are under tension during use of the strap; and
   at least one guide cooperating with the elastic cord, wherein at least a portion of the elastic cord slidably passes through the at least one guide, the at least one guide adapted to rest adjacent of a wearer of the wearer of the article; and
   wherein the at least one guide is flexible so as to conform to a wearer of the article.

2. The strap of claim 1, wherein at least the first end of the elastic cord is fixed to the cord lock.

3. The strap of claim 1, wherein the elastic cord includes a first portion and second portion, wherein the first portion and the second portion are substantially parallel to one another.

4. The strap of claim 1, wherein the cord lock includes at least two spaced apart locking portions constructed and arranged to selectively anchor and release segments of the cord as the cord passes through the locking portion.

5. The strap of claim 1, wherein the at least one guide spaces portions of the elastic cord from one another.

6. The strap of claim 1, in combination with the article, wherein the article is eyewear.

7. The strap of claim 1, in combination with the article, wherein the article is an article of clothing.

8. The strap of claim 1, wherein the elastic cord comprises a circular cross-section.

9. An adjustable length strap for use with an article, the strap comprising:
   at least one elastic cord having first and second ends;
   at least one cord lock cooperating with the elastic cord such that the elastic cord is slidable through the cord lock to selectively adjust the length of the strap, the first and second ends of the cord are connected to the article or to the cord lock, or the first end is connected to the cord lock and the second end is connected to the article such that substantially all sections of the cord are under tension during use of the strap; and
   at least one guide cooperating with the elastic cord, wherein at least a portion of the elastic cord slidably passes through the at least one guide, the at least one guide adapted to rest adjacent of a wearer of the article,
   wherein the strap includes at least two elastic cords and at least two cord locks with the at least one guide provided between the cord locks, each elastic cord slidably passing at least once through at least one of the cord locks and each elastic cord having at least the first end fixed to one of the cord locks.

10. The strap of claim 9, wherein the elastic cords slidably pass through different cord locks.

11. The strap of claim 9, wherein the cord locks are separated by a distance and the strap length is selectively adjustable by moving at least one cord lock along the cord relative to the other cord lock to change the distance between the cord locks.

12. The strap of claim 9, wherein both cord locks are unlocked to selectively adjust the length of the strap.

13. An adjustable length strap for use with an article, the strap comprising:
   at least one cord having first and second ends;
   at least one cord lock cooperating with the elastic cord such that at least a portion of the cord is slidable through the cord lock to selectively adjust the length of the strap; and
   at least one guide cooperating with the cord, wherein at least a portion of the cord slidably passes through the at least one guide, the at least one guide adapted to rest adjacent a wearer of the article,
   wherein at least the first end of the cord is fixed to the cord lock, while said at least one portion is slidable therethrough; and
   wherein the at least one guide is flexible so as to conform to a wearer of the article.

14. The strap of claim 13, wherein the cord includes a first portion and second portion, wherein the first portion and the second portion are substantially parallel to one another.

15. The strap of claim 13, wherein the cord lock includes at least two spaced apart locking portions constructed and arranged to selectively anchor and release segments of the cord.

16. The strap of claim 13, wherein the at least one guide spaces portions of the cord from one another.

17. The strap of claim 13, wherein the strap includes at least two cords and at least two cord locks with the at least one guide provided between the cord locks, each cord slidably passing at least once through at least one of the cord locks and each cord having at least the first end fixed to one of the cord locks.

18. The strap of claim 17, wherein the cords slidably pass through different cord locks.

19. The strap of claim 17, wherein the cord locks are separated by a distance and the strap length is selectively adjustable by moving at least one cord lock along the cord relative to the other cord lock to change the distance between the cord locks.

20. The strap of claim 17, wherein both cord locks are unlocked to selectively adjust the length of the strap.

21. The strap of claim 13, in combination with the article, wherein the article is eyewear.

22. The strap of claim 13, in combination with the article, wherein the article is an article of clothing.

23. The strap of claim 13, wherein the cord comprises a circular cross-section.

24. An adjustable length strap for an article, the strap comprising:
   at least one elastic cord having first and second ends;
   at least one cord lock cooperating with the elastic cord such that the elastic cord is slidable through the cord lock to selectively adjust the length of the strap, the cord and cord lock lying substantially within a plane that is conformable to a wearer of the article; and
   at least one guide cooperating with the elastic cord, wherein the elastic cord slidably passes through the at least one guide, the at least one guide adapted to rest adjacent of a wearer of the article; and
   wherein the at least one guide is flexible so as to conform to a wearer of the article.

25. The strap of claim 24, wherein at least the first end of the elastic cord is fixed to the cord lock.

26. The strap of claim 24, wherein the elastic cord includes a first portion and second portion, wherein the first portion and the second portion are substantially parallel to one another.

27. The strap of claim 24, wherein the cord lock includes at least two spaced apart locking portions constructed and arranged to selectively anchor and release segments the cord as the cord passes through the locking portion.

28. The strap of claim 24, wherein the at least one guide spaces at least portions of the elastic cord from one another.

29. The strap of claim 24, wherein the strap includes at least two elastic cords and at least two cord locks with the at least one guide provided between the cord locks, each elastic cord slidably passing at least once through at least one of the cord locks and each elastic cord having at least the first end fixed to one of the cord locks.

30. The strap of claim 29, wherein the elastic cords slidably pass through different cord locks.

31. The strap of claim 29, wherein the cord locks are separated by a distance and the strap length is selectively adjustable by moving at least one cord lock along the cord relative to the other cord lock to change the distance between the cord locks.

32. The strap of claim 29, wherein both cord locks are unlocked to selectively adjust the length of the strap.

33. The strap of claim 24, in combination with the article, wherein the article is eyewear.

34. The strap of claim 24, in combination with the article, wherein the article is an article of clothing.

35. The strap of claim 24, wherein the cord lock includes a body having a width and a thickness, wherein the thickness is less than the width such that the body is generally flat.

36. The strap of claim 24, wherein the at least one elastic cord is routed in a manner such that all segments of the elastic cord lie in the same plane.

37. An adjustable length strap for use with an article, the strap comprising:
 at least one elastic cord having first and second ends;
 at least one cord lock cooperating with the elastic cord such that the length of the strap is selectively adjustable by movement of the elastic cord through the cord lock; and
 a guide provided on the elastic cord, the elastic cord being movable through the guide; wherein the guide is flexible so as to conform to a wearer of the article.

38. The strap of claim 37, wherein at least one end of the elastic cord is fixed to the cord lock.

39. The strap of claim 37, wherein the elastic cord includes a first portion and a second portion, wherein the first portion and second portion are substantially parallel to one another.

40. The strap of claim 37, wherein the guide spaces portions of the elastic cord from one another.

41. The strap of claim 37, wherein the strap includes at least two elastic cords and at least two cord locks with the guide provided between the cord locks, each elastic cord slidably passing at least once through at least one of the cord locks and each elastic cord having at least the first end fixed to one of the cord locks.

42. The strap of claim 41, wherein the elastic cords slidably pass through different cord locks.

43. The strap of claim 41, wherein the cord locks are separated by a distance and the strap length is selectively adjustable by moving at least one cord lock along the cord relative to the other cord lock to change the distance between the cord locks.

44. The strap of claim 41, wherein both cord locks are unlocked to selectively adjust the length of the strap.

45. The strap of claim 37, in combination with the article, wherein the article in eyewear.

46. The strap of claim 37, in combination with the article, wherein the article in an article of clothing.

47. An adjustable length strap for an article, the strap comprising:
 at least one elastic cord having first and second ends;
 at least two cord locks separated by a distance and cooperating with the elastic cord such that the elastic cord is slidable through the cord locks; and
 at least one guide cooperating with the elastic cord, wherein at least portions of the elastic cord slidably pass through at least one guide, the length of the strap is selectively adjustable by movement of the elastic cord through the cord lock guide adapted to rest adjacent a wearer of the article,
 wherein the length of the strap may be adjusted by moving at least one cord lock to vary the distance between the cord locks.

48. The strap of claim 47, wherein at least the first end of the elastic cord is fixed to the cord lock.

49. The strap of claim 47, wherein the elastic cord includes a first portion and second portion, wherein the first portion and the second portion are substantially parallel to one another.

50. The strap of claim 47, wherein at least one of the cord locks includes at least two spaced apart locking portions constructed and arranged to selectively anchor and release segments of the cord as the cord passes through the locking portion.

51. The strap of claim 47, wherein the at least one guide spaces at least portions of the elastic cord from one another.

52. The strap of claim 47, wherein the strap includes at least two elastic cords and with the at least one guide provided between the cord locks, each elastic cord slidably passing at least once through at least one of the cord locks and each elastic cord having at least the first end fixed to one of the cord locks.

53. The strap of claim 52, wherein the elastic cords slidably pass through different cord locks.

54. The strap of claim 52, wherein both cord locks are unlocked to selectively adjust the length of the strap.

55. The strap of claim 47, in combination with the article, wherein the article is eyewear.

56. The strap of claim 47, in combination with the article wherein the article is an article of clothing.

57. An adjustable length strap for an article, the strap comprising:
 at least two elastic cords having first and second ends; and
 at least two cord locks cooperating with the elastic cords such that the elastic cords are slidable through the cord locks to adjust the length of the strap,
 wherein at least the first ends of the elastic cords are fixed to a respective cord lock and at least one segment of each cord passes through at least one cord lock.

58. The strap of claim 57, wherein the elastic cords include a first portion and second portion, wherein the first portion and the second portion are substantially parallel to one another.

59. The strap of claim 57, wherein at least one of the cord locks includes at least two spaced apart locking portions constructed and arranged to selectively anchor and release segments of the cords as the cords pass through the locking portions.

60. The strap of claim 57, further comprising at least on guide cooperating with the at lease one elastic cord, wherein the at least one elastic cord slidably passes through the at least one guide, the at least one guide adapted to rest adjacent the head of a wearer.

61. The strap of claim 60, wherein the at least one guide spaces at least portions of the elastic cords from one another.

62. The strap of claim 60, wherein the at least one guide is provided between the cord locks, each elastic cord slidably passing at least once through at least one of the cord locks and each elastic cord having at least the first end fixed to one of the cord locks.

63. The strap of claim 62, wherein the elastic cords slidably pass through different cord locks.

64. The strap of claim 57, wherein the cord locks are separated by a distance and the strap length is selectively adjustable by moving at least one cord lock along the cord relative to the other cord lock to change the distance between the cord locks.

65. The strap of claim 57, wherein both cord locks are unlocked to selectively adjust the length of the strap.

66. The strap of claim 57, in combination with the article, wherein the article is eyewear.

67. The strap of claim 57, in combination with the article wherein the article is an article of clothing.

* * * * *